United States Patent
Mertelmeier et al.

(10) Patent No.: US 7,742,558 B2
(45) Date of Patent: Jun. 22, 2010

(54) MAMMOGRAPHY TOMOSYNTHESIS APPARATUS WITH A COMPRESSION PLATE HAVING A RECESS THEREIN

(75) Inventors: Thomas Mertelmeier, Erlangen (DE); Wei Zhao, East Setauket, NY (US)

(73) Assignees: Siemens Aktiengesellschaft, Munich (DE); Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/437,957

(22) Filed: May 8, 2009

(65) Prior Publication Data
US 2010/0111249 A1    May 6, 2010

(30) Foreign Application Priority Data
Nov. 4, 2008    (DE) .................. 10 2008 055 737

(51) Int. Cl.
*A61B 6/00* (2006.01)

(52) U.S. Cl. .......................................... 378/21; 378/37
(58) Field of Classification Search ............. 378/20–27, 378/37
See application file for complete search history.

(56) References Cited

U.S. PATENT DOCUMENTS

| 7,302,031 B2 | 11/2007 | Hjärn et al. ................... 378/37 |
| 2007/0280412 A1 | 12/2007 | Defreitas et al. .............. 378/37 |
| 2008/0043904 A1 | 2/2008 | Hoernig ....................... 378/37 |

*Primary Examiner*—Courtney Thomas
(74) *Attorney, Agent, or Firm*—Schiff Hardin LLP

(57) ABSTRACT

A tomosynthesis apparatus for mammography has an x-ray source for emission of x-ray beams from different directions directed toward a detector, and a compression plate and a support plate arranged in the beam path between the x-ray source and the detector. A breast to be examined is positioned and compressed between the compression plate and the support plate. The compression plate exhibits a concave recess open in the direction of the support plate on the side of the compression plate facing toward the support plate.

15 Claims, 2 Drawing Sheets

MAMMOGRAPHY TOMOSYNTHESIS APPARATUS WITH A COMPRESSION PLATE HAVING A RECESS THEREIN

BACKGROUND OF THE INVENTION

1. Field of the Invention

The present invention concerns a tomosynthesis apparatus of the type having a compression plate and a support plate.

2. Description of the Prior Art

A tomosynthesis is an examination of the breast (in particular the female breast) that is conducted with the goal of detecting tumors in as early a stage as possible. Through continuous improvement of the imaging methods it is sought to generate images with high significance in order to be able to differentiate benign variations from malignant variations with high certainty. One goal in the improvement of the imaging methods is to reduce the number of erroneous findings, i.e. the number of suspected findings that are not caused by malignant variations and the number of undetected tumors.

During the tomosynthesis the breast is positioned between a support plate and a compression plate in a tomosynthesis apparatus, and is compressed. The breast is subsequently irradiated from different directions with x-rays emitted by an x-ray source, so the individual projections forming a tomosynthesis image data set are acquired. A tomosynthetic 3D x-ray image is calculated in a known manner from these projections using a reconstruction algorithm.

In tomosynthesis examinations it has been observed on different occasions that the breast was not completely imaged. In other words, in some cases it was not possible to generate a complete tomosynthesis 3D x-ray image of the entire breast in the reconstruction.

SUMMARY OF THE INVENTION

It is the object of the present invention to specify a tomosynthesis apparatus with which the tomosynthesis examination of the breast is improved by avoiding incomplete data acquisition that results in an inability to implement a complete tomosynthesis.

This object is achieved in accordance with the invention by a tomosynthesis apparatus having an x-ray source that emits an x-ray beam directed at a detector, and a compression plate and a support plate that are arranged in the beam path between the x-ray source and the detector. A breast to be examined is positioned and compressed between the compression plate and the support plate. On its side facing toward the support plate, the compression plate has a concave recess that is open in the direction of the support plate.

The design of the tomosynthesis apparatus according to the invention is based on the following insight:

Conventional tomosynthesis apparatuses use compression systems composed of a support plate and a compression plate that are also used for conventional mammography. The invention is based on the recognition that, in a comparison between tomosynthesis and mammography (assuming that the respective apparatuses that are used have the same acquisition geometry, thus in particular the same focus-detector distance), the examination volume accessible to the tomosynthesis is smaller than the volume that can be examined with conventional mammography. In the case of tomosynthesis, "examination volume" means the volume that can be completely imaged in all projections acquired in the tomosynthesis examination. In the case of conventional mammography, the examination volume is the volume that is irradiated by the x-ray beam used for acquisition of the projection.

Starting from the realization that tomosynthesis and mammography exhibit examination volumes of different sizes, the invention is based on the further insight that, given a compression system as used for conventional mammography, a portion of the breast lies outside of the examination volume accessible to the tomosynthetic examination when as this compression system is used in the tomosynthesis.

This problem is solved according to the invention by the use of a compression plate for tomosynthesis drains that has a concave recess open in the direction of the support plate on this side of the compression plate facing toward the bearing plate. The breast to be examined is accommodated in the concave recess of the compression plate, this being shaped in a specific manner. In conventional mammography, the breast is primarily compressed with the use of a central force acting essentially perpendicular to the detector surface. The breast is primarily compressed in the central region of the breast. In contrast to this, the breast, in the system according to the invention, is also compressed and positioned by a force acting laterally on the breast. This leads to the situation that the breast tissue is pushed into a central region of the support plate or the compression plate. Such a deformation and compression leads to an improvement in the tomosynthesis imaging of the breast; the probability that a portion of the breast lies outside of the accessible examination volume is significantly less.

In comparison to conventional compression systems, the use of a compression plate with a concave recess leads to less compression of the breast. The invention is based on the insight that this effect, which is disadvantageous for conventional mammography, is far less disadvantageous for tomosynthesis, and even entails advantages.

In conventional mammography, a high compression of the breast is sought in order to press the breast tissues as far apart from one another as possible so that an overlapping (occlusion) of individual structures that possibly conceal one another can be avoided in the generated mammography image. This problem does not exit in tomosynthesis since a tomosynthetic 3D x-ray image, in which structures lying atop one another even in a direction perpendicular to the detector surface can be detected, is calculated from the multiple acquired individual projections.

An additional reason why high compression of the breast that is sought in mammography is the fact that the scatter radiation occurring in the mammographic image is proportional to the thickness of the irradiated tissue. However, the invention is based on the insight that the reconstruction algorithm used in tomosynthesis to reconstruct the tomosynthetic 3D x-ray image effectively compensates for the scatter radiation that occurs in the individual projections. For this reason, the greater thickness of the irradiated tissue (due to the lower compression) does not negatively affect the scatter radiation proportion in the resulting tomosynthetic 3D x-ray image.

The 3D x-ray images tomosynthetically generated in a tomosynthesis exam, moreover, exhibit a significantly higher resolution in a plane parallel to that of the detector (typically a flat panel detector is used for the tomosynthesis) than in a direction perpendicular to this plane. A lower compression of the breast is thus also advantageous for this reason. Variations of the breast (for example, lesions) that extend perpendicularly to the surface of the detector can be better and more certainly detected in this way. Moreover, the lower compression is perceived to be less uncomfortable by the patient.

In summary, by the use of a compression plate with a concave recess the breast can be brought into that volume which is designated as an accessible examination volume for a tomosynthetic examination. The lower compression of the breast in comparison to mammography does not negatively affect the tomosynthesis, in contrast to mammography.

DESCRIPTION OF THE PREFERRED EMBODIMENTS

Figure 1:
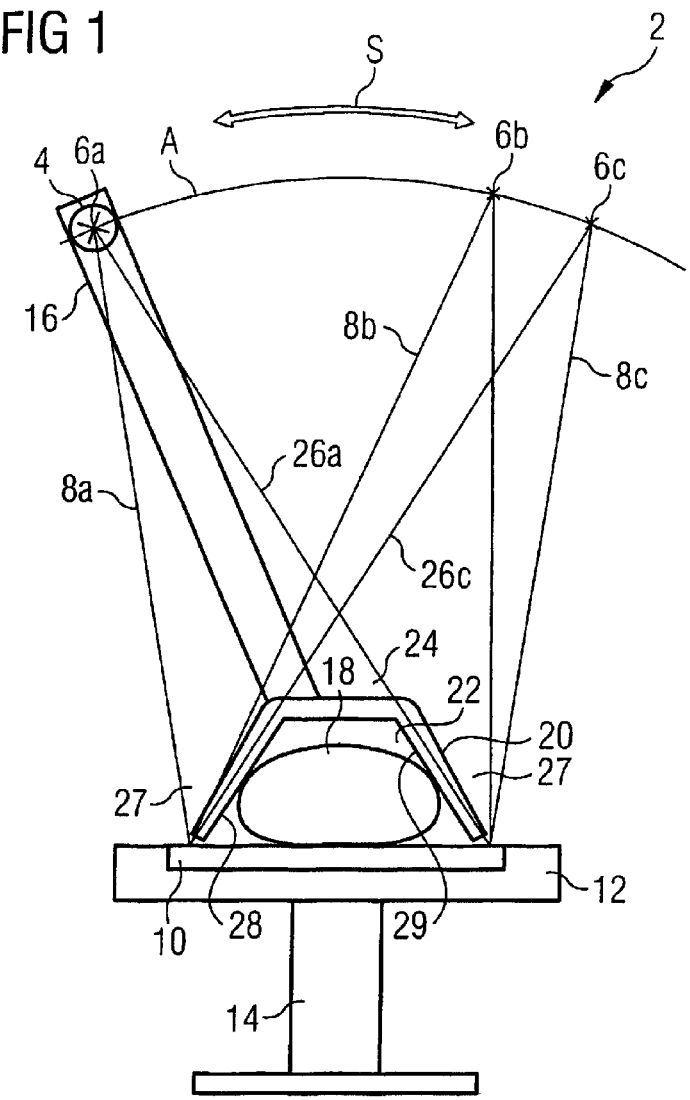
FIG. 1 schematically illustrates a first embodiment of a tomosynthesis mammography apparatus, in a front view, in accordance with the present invention.

FIG. 1 shows a first embodiment of a tomosynthesis apparatus 2 in a schematic frontal view. The tomosynthesis apparatus 2 has an x-ray source 4 with a focus from which x-ray beams 8a ... 8c emanate that are directed toward a flat panel detector 10 that is recessed in a support plate 12. A vertical column 14 supports the tomosynthesis apparatus 2.

The x-ray source 4 is mounted on a pivot arm 16 that produces a motion causing the focus of the x-ray source 4 to be moved in a scanning range (which is typically between 15° and 30°) in a scan direction S on a scanning path A. FIG. 1 exemplarily shows three different focus positions 6a, 6b and 6c that the focus of the x-ray source 4 can occupy during a scan procedure. FIG. 1 likewise shows the respective x-ray beams 8a, 8b and 8c that emanate from the focus of the x-ray source 4 when it is located at the focus positions 6a, 6b and 6c. The focus of the x-ray source 4 adopts the focus positions 6a and 6c when the x-ray source 4 is located at its first and second end positions of the scanning range, respectively.

The movement of the focus of the x-ray source 4 need not follow the path shown in FIG. 1 (which path approximately corresponds to the segment of a circular orbit). The movement of the focus can alternatively ensue along a straight line, for example. Such a straight-line movement of the x-ray focus can ensue by displacement of the x-ray source 4 along a suitable frame; alternatively, the x-ray source 4 can be of the type known as a multi-focus x-ray source, whose single emitter is activated in succession along the scan direction S, such that in this case the focus of the x-ray source 4 is also displaced along a straight line.

A breast 18 (which serves as an examination subject), positioned and compressed on the bearing plate 12 is irradiated from various directions with the x-ray beams 8a through 8c. To conduct a tomosynthetic examination with the use of a compression plate 20, the breast 18 is compressed and positioned between this compression plate 20 and the support plate 12. The compression plate 20 has a concave recess 22 that is open in the direction of the support plate 12 on its side facing toward the support plate 12, in which recess 22 the breast 18 is accommodated. The compression plate 20 or its recess 22 is advantageously dimensionally stable, meaning that the shape of the recess 22 is essentially identical in the loaded state (the breast 18 is compressed) and in the unloaded state (the breast 18 is not compressed). The shape of the concave recess 22 (more precisely stated, its inner contour) recessed into the compression plate 20 essentially conforms with the shape of the examination volume 24 accessible with the use of the tomosynthesis apparatus 2. The shape of the recess 22 is advantageously selected so that this volume lies entirely within the examination volume 24 accessible to the tomosynthetic examination.

The contour of the surface facing toward the bearing plate 12, i.e. the inner contour of the recess 22 of the compression plate 20, is advantageously adapted to the outer contour of the accessible examination volume 24. This is apparent in the curve of the sides 28, 28 of the compression plate 20 shown in FIG. 1.

The accessible examination volume 24 is that volume which is recorded by each of the projections that are acquired during the acquisition of a tomosynthetic image data set. In other words, the accessible examination volume can generally be defined as follows. The x-ray source 4 of the tomosynthesis apparatus 2 (more precisely stated, the focus of the x-ray source 4) is movable in a scanning range between the first and a second end position. The accessible examination volume 24 is defined by an overlap region between a first x-ray beam 8a (which can be emitted by the x-ray source 4 in a first end position) and a second x-ray beam 8c (which can be emitted by the x-ray source 4 in a second end position).

In the schematic frontal view selected for FIG. 1, the x-ray beams 8a ... 8c emanating from the individual focus positions 6a ... 6c appear as triangles. These are thereby slices through the x-ray beams 8a ... 8c which in reality are nearly conical. The examination volume 24 accessible to the tomosynthetic examination is bounded by the x-ray beams 8a and 8c that emanate from the x-ray source 4 when this is located in its first (i.e. left) or, respectively, second (i.e. right) end position of the scanning range. The examination volume 24 is correspondingly bounded on one side by the right boundary ray 26a of the x-ray beam 8a and on the other side by the left boundary ray 26c of the x-ray beam 8c.

The shape of the compression plate 20 is now presently selected so that the breast 18 in its compressed state is located entirely inside the accessible examination volume 24. Otherwise the danger would exist that the breast 18 would not be completely imaged in the acquired tomosynthetic 3D x-ray image. Given the use for tomosynthesis of conventional compression plates as are known from mammography, the risk exists that a portion of the breast 18 would not be present in all projections; in other words, not all side regions 27 accessible to the emitted x-ray beams 8a ... 8c during the scan movement would be compressed. In these side regions 27, the breast tissue is imaged by only some but not all x-ray beams 8a ... 8c emitted during the scan movement. Since the portion of the breast 18 situated in the side regions 27 is not imaged in all acquired projections, a complete tomosynthetic 3D x-ray image of this part of the breast 18 cannot be reconstructed.

The shape or contour of the recess 22 can be freely selected in principle under consideration of the aforementioned condition that the breast 18 in the compressed state should lie entirely within the accessible examination volume 24. In the exemplary embodiment shown in FIG. 1, the surface contour of the concave recess 22 of the compression plate 20 is selected such that this at least partially corresponds to the shape of the accessible examination volume 24. The internal contour of the recess 22 in the region in the region of its sides 28 and 29 thereby follows the curve of the boundary rays 26a and 26c that limit the accessible examination volume 24.

If the breast 18 is now compressed with the use of the compression plate 20, a force acts on the breast 18 from the sides 28, 29 of the compression plate 20, this force laterally acting on the breast 18. The breast 18 is pushed into the center of the flat panel detector 10 instead of to the side as in conventional mammography systems.

Figure 2:
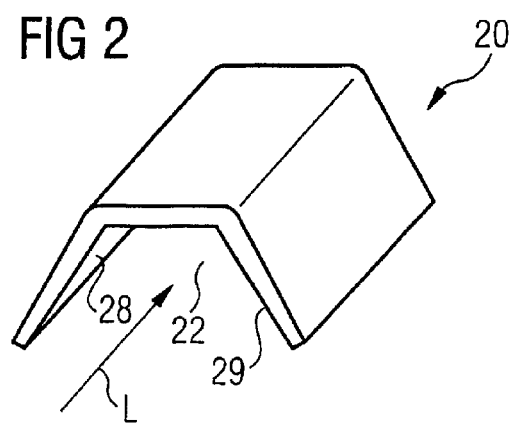
FIG. 2 is a perspective view of a first embodiment of a compression plate in accordance with the present invention.

FIG. 2 shows the compression plate 20 known from FIG. 1 in a schematic perspective view. The compression plate 20 extends in the manner of a channel in a longitudinal extension direction L. The longitudinal extension direction L of the compression plate 20 is oriented perpendicular to a chest wall plane that in turn stands perpendicular to the bearing plate 12 (see FIG. 1). For a patient the tomosynthesis apparatus 2 is accessible from the side of the chest wall, for example, for placement of the breast 18 on the bearing plate 12. The compression plate 20 exhibits a concave inner contour in a slice plane perpendicular to the longitudinal extension direction L, which inner contour exhibits the shape of a trapezoid.

The compression plate 20 shown in FIG. 2 is produced without metallic components; furthermore, this advantageously consists entirely of a plastic material. Metallic components (for example a frame or braces) can hinder the exposure of the breast 18 in the scope of the implementation of a tomosynthetic examination. The omission of metallic components is therefore advantageous. The compression plate is advantageously produced from polycarbonate or PET. The compression plate 20 shown in FIG. 2 is advantageously dimensionally stable, meaning that its shape varies only very insignificantly between a loaded state in which the breast is compressed and an unloaded state in which the breast is unloaded.

Figure 3:
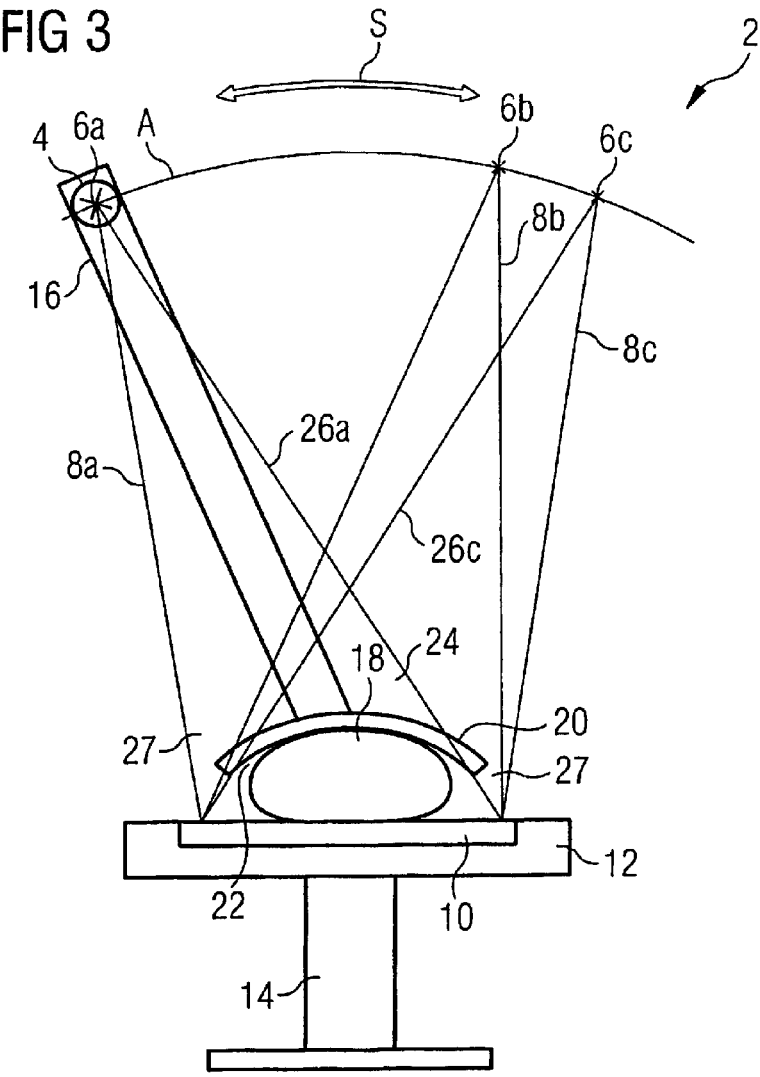
FIG. 3 schematically illustrates a second embodiment of a tomosynthesis mammography apparatus, in a front view, in accordance with the present invention.

FIG. 3 shows an additional exemplary embodiment for a tomosynthesis apparatus 2. This is in principle designed just like the apparatus shown in FIG. 1 but, in contrast to this, does not have a rigid, dimensionally stable compression plate 20 but rather a partially flexible compression plate 20. Its concave recess 22 has a rounded curve when considered in a slice plane perpendicular to its longitudinal extension direction L.

Figure 4:
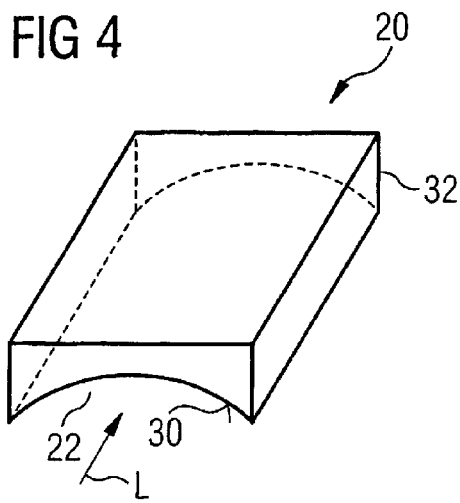
FIG. 4 is a perspective view of a second embodiment of a compression plate in accordance with the present invention.

FIG. 4 shows a perspective detail view of this compression plate 20 with which the tomosynthesis apparatus 2 shown in FIG. 3 is equipped. The contour of the inner surface 30 of the compression plate 20 (which, in the installed state, faces towards the bearing plate 12) essentially corresponds to a segment of a generated cylinder surface. The cylinder upon which the generated cylinder surface is based is a circular cylinder in the shown exemplary embodiment. However, the cylinder upon which the cylinder surface is based can likewise be a parabolic or elliptical cylinder.

The compression plate 20 shown in FIG. 1 is reversibly (thus predominantly elastically) deformable, wherein this always exhibits a concave recess 22 both in the unloaded and in the loaded state. The compression plate 20 moreover has an edge 32 which, in the installed state, extends essentially perpendicular to the planning level of the bearing plate 12 and connects over its entire circumference to the inner surface 30 of the compression plate 20. This edge 32 serves to improve the stability of the compression plate 20. The compression plate 20 is advantageously produced from various materials: an elastic material (for example an x-ray-transparent elastomer) on its underside facing towards the breast 18 and a rigid/solid material (for example polycarbonate or PET) for the edge 32. The compression plate shown in FIG. 4 also extends in a channel shape in a longitudinal extension direction L oriented perpendicular to the chest wall side.

As explained in connection with FIG. 1, it is also shown in FIG. 4 that the compression plate 20 is shaped such that, in the compressed state, the breast 18 is entirely situated within the accessible examination volume 24. Depending on the shape and size of the breast 18 to be examined, the tomosynthesis apparatuses 2 shown in FIGS. 1 and 3 can be equipped with a compression plate 20 that has a recess 22 that is adapted to the shape and size of the breast 18. This applies both for the compression plate 20 shown in FIG. 2 and for the compression plate 20 shown in FIG. 4.

Although modifications and changes may be suggested by those skilled in the art, it is the intention of the inventors to embody within the patent warranted hereon all changes and modifications as reasonably and properly come within the scope of their contribution to the art.

We claim as our invention:

1. A tomosynthesis mammography apparatus comprising;
   an x-ray source that emits an x-ray beam;
   a radiation detector on which said x-ray beam is incident;
   a compression plate and a support plate located between said x-ray source and said radiation detector in a beam path of said x-ray beam, said compression plate and said support plate being configured to retain and compress a breast therebetween;
   said x-ray source being configured to emit said x-ray beam to irradiate the breast between the compression plate and the support plate from a plurality of different directions, and said radiation detector being configured to detect x-rays in said x-ray beam, attenuated by the breast between said compression plate and support plate, from each of said different directions to generate a plurality of projection images of the breast;
   said compression plate having a side facing said support plate, which is in contact with said breast, and having a concave recess in said side that accommodates the breast therein; and
   a processor supplied with said projection images configured to execute a reconstruction algorithm to generate a 3D tomosynthesis image of the breast from said projection images.

2. A tomosynthesis apparatus as claimed in claim 1 wherein said compression plate is dimensionally stable.

3. A tomosynthesis apparatus as claimed in claim 1 wherein said compression plate is reversibly deformable between an unloaded state wherein the breast is not compressed and a loaded state wherein the breast is compressed, and wherein said compression plate exhibits said concave recess both in said unloaded state and in said loaded state.

4. A tomosynthesis apparatus as claimed in claim 1 wherein said x-ray source irradiates a volume of the breast with said x-ray beam in each of said projection images, the respective volumes in said projection images, collectively and in combination, defining a tomosynthetic examination volume, and wherein said recess of said compression plate is situated entirely within said tomosynthetic examination volume.

5. A tomosynthesis apparatus as claimed in claim 1 wherein said concave recess of said compression plate has a surface contour facing said support plate conforming to at least a portion of a contour of said tomosynthetic examination volume.

6. A tomosynthesis apparatus as claimed in claim 5 wherein concave recess of said compression plate has a longitudinal extent in a direction proceeding perpendicularly from a chest wall plane of an examination subject whose breast is being irradiated.

7. A tomosynthesis apparatus as claimed in claim 6 wherein said recess of said compression plate has a concave inner contour as seen in a slice plane perpendicular to said longitudinal extent.

8. A tomosynthesis apparatus as claimed in claim 7 wherein an inner side of the concave recess of said compression plate has a rounded curve as seen in said slice plane perpendicular to said longitudinal extent.

9. A tomosynthesis apparatus as claimed in claim 8 wherein said inner side of said concave recess has a shape substantially corresponding to a segment of a cylinder surface.

10. A tomosynthesis apparatus as claimed in claim 9 wherein said inner side of said concave recess has a shape corresponding to a segment of a surface of a cylinder selected from the group consisting of a circular cylinder, a parabolic cylinder, and an elliptical cylinder.

11. A tomosynthesis apparatus as claimed in claim 6 wherein said concave recess has an inner side having a trapezoidal shape as seen in a slice plane perpendicular to said longitudinal extent.

12. A tomosynthesis apparatus as claimed in claim 6 wherein said concave recess of said compression plate has a shape corresponding to a channel in a direction along said longitudinal extent.

13. A tomosynthesis apparatus as claimed in claim 1 wherein said compression plate has an edge oriented substantially perpendicularly to said support plate.

14. A tomosynthesis apparatus as claimed in claim 1 wherein said compression plate is composed of non-metallic components.

15. A tomosynthesis apparatus as claimed in claim 1 wherein said compression plate is comprised of a plastic material.

* * * * *